United States Patent
Parthasaradhi et al.

(10) Patent No.: US 7,456,181 B2
(45) Date of Patent: Nov. 25, 2008

(54) ARIPIPRAZOLE CRYSTALLINE FORMS

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Kesireddy Subash Chander, Hyderabad (IN)

(73) Assignee: Hetero Drugs Limited, Andhrapradesh (IN)

( * ) Notice: Subject to any disclaimer, the term of this patent is extended or adjusted under 35 U.S.C. 154(b) by 487 days.

(21) Appl. No.: 10/518,214

(22) PCT Filed: Jul. 25, 2003

(86) PCT No.: PCT/IN03/00251

§ 371 (c)(1),
(2), (4) Date: Dec. 16, 2004

(87) PCT Pub. No.: WO2005/009990

PCT Pub. Date: Feb. 3, 2005

(65) Prior Publication Data

US 2005/0234071 A1   Oct. 20, 2005

(51) Int. Cl.
*C07D 401/12* (2006.01)
*A61K 31/497* (2006.01)

(52) U.S. Cl. .................................... 514/253; 544/363
(58) Field of Classification Search ................ 514/253; 544/363
See application file for complete search history.

(56) References Cited

U.S. PATENT DOCUMENTS 5,006,528 A    4/1991   Oshiro et al.

FOREIGN PATENT DOCUMENTS

EP   367 141       5/1990
WO   WO 03/026659   4/2003

OTHER PUBLICATIONS

PCT International Search Report dated Jul. 25, 2003.
Japanese Unexamined Patent Publication No. 191256.
Satoshi Aoki et al. "Study on Crystal Transformation of Aripiprazol" in the Fourth Japan—Korea Symposium on Separation Technology. The Korean Institute of Chemical Engineers, Oct. 1996, CR 119, pp. 937-940.

*Primary Examiner*—James O. Wilson
*Assistant Examiner*—Ebenezer Sackey
(74) *Attorney, Agent, or Firm*—Caesar, Rivise, Bernstein, Cohen & Pokotilow, Ltd.

(57) ABSTRACT

The present invention provides novel crystalline forms of aripiprazole and processes for their preparation.

3 Claims, 3 Drawing Sheets

ARIPIPRAZOLE CRYSTALLINE FORMS

FIELD OF THE INVENTION

The present invention provides novel crystalline forms of aripiprazole and processes for their preparation.

BACKGROUND OF THE INVENTION

Aripiprazole of formula (1):

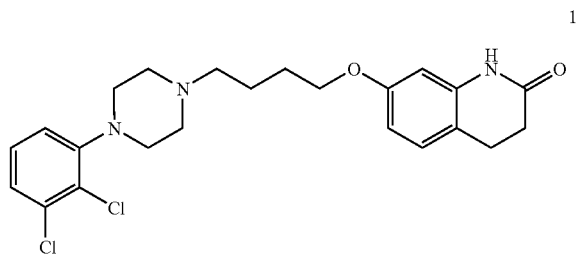

1 or 7-[4-[4-(2,3-Dichlorophenyl)-1-piperazinyl]butoxy]-3,4-dihydro-2(1H)-quinolinone and its salts are useful for treating schizophrenia and their therapeutic uses were disclosed in U.S. Pat. No. 5,006,528.

Processes for the preparation of aripiprazole and its salts were described in U.S. Pat. No. 5,006,528. Various crystalline forms of aripiprazole and its hydrates were disclosed in WO 03/026659, Japanese Unexamined Patent Publication No. 191256/1990 and 4$^{th}$ Japanese-Korean Symposium on Separation Technology (Oct. 6-8, 1996).

We have discovered a novel crystalline form of aripiprazole, aripiprazole methanolate and aripiprazole ethylene dichloride solvate. The novel crystalline form of aripiprazole is non hygroscopic, do not have the tendency to convert to other forms and suitable for pharmaceutical preparations.

The methanolate and ethylene dichloride solvate are non-hygroscopic, obtainable in pure form and can be converted to crystalline forms of aripiprazole and aripiprazole hydrates.

Therefore, the solvates are useful as intermediates for preparing pure aripiprazole or aripiprazole hydrates in any crystalline form.

Thus, one object of the present invention is to provide stable, non-hygroscopic crystalline form of aripiprazole, process for preparing this form and pharmaceutical compositions containing it.

Another object of the present invention is to provide aripiprazole methanolate and aripiprazole ethylenedichloride solvate and process for preparing the solvates; and use of these solvates to prepare other forms of aripiprazole.

DESCRIPTION OF THE INVENTION

In accordance with the present invention, there is provided a novel crystalline form of aripiprazole. The crystalline form is designated as aripiprazole form III and typical form III x-ray powder diffraction spectrum of aripiprazole form III is shown in FIG. 1.

Aripiprazole form III is characterized by peaks in the powder x-ray diffraction spectrum having 2θ angle positions at about 8.8, 11.2, 11.4, 11.9, 13.6, 14.4, 15.0, 15.9, 16.4, 17.8, 18.7, 20.4, 20.8, 21.4, 22.2, 23.5, 25.0, 25.9 and 26.5 degrees.

In accordance with the present invention, there is provided a process for preparation of the aripiprazole form III comprising the steps of:

a) preparing a solution of aripiprazole in a mixture of methyl tert-butyl ether, acetonitrile and tetrahydrofuran; and
b) isolating aripiprazole form III from the solution.

Aripiprazole used in the process can be in any of the crystalline forms. Aripiprazole solvate or hydrate form can also be used in the process to produce aripiprazole form III.

The solution of aripiprazole is usually prepared at elevated temperature, preferably at reflux temperature and then the solution is cooled preferably to 0° C. to 30° C., more preferably to 15° C. to 30° C. The precipitated form III crystals are collected by filtration or centrifugation.

In accordance with the present invention, there is provided aripiprazole methanolate. The content of methanol is between about 2 to 6% of the weight of aripiprazole methanolate. Aripiprazole methanolate typically shows a crystalline form, which is designated as aripiprazole methanolate form IV and typical form IV x-ray powder diffraction spectrum of aripiprazole methanolate form IV is shown in FIG. 2.

Aripiprazole methanolate form IV is characterized by peaks in the powder x-ray diffraction spectrum having 2θ angle positions at about 9.8, 11.0, 11.8, 12.1, 12.6, 13.6, 17.4, 18.8, 20.1, 23.3, 24.6, 25.0, 25.9, 27.2, 28.4, 29.3, 30.1 and 31.5 degrees.

In accordance with the present invention, there is provided a process for preparation of the aripiprazole methanolate form IV comprising the steps of:

a) preparing a solution of aripiprazole in a mixture of methanol and tetrahydrofuran; and
b) isolating aripiprazole methanolate form IV from the solution.

The solution of aripiprazole is usually prepared at elevated temperature, preferably at reflux temperature and then the solution is cooled preferably to 0° C. to 30° C. The precipitated form IV crystals are collected by filtration or centrifugation.

Aripiprazole methanolate can be used to prepare aripiprazole forms by crystallizing from the appropriate solvent system. Thus, for example aripiprazole form III can be prepared by preparing a solution of aripiprazole methanolate in a mixture of methyl tert-butyl ether, acetonitrile and tetrahydrofuran and isolating aripiprazole form III from the solution.

In accordance with the present invention, there is provided aripiprazole ethylenedichloride solvate. The content of ethylenedichloride is between about 15 to 40% of the weight of aripiprazole ethylenedichloride solvate. Aripiprazole ethylenedichloride solvate typically shows a crystalline form, which is designated as aripiprazole ethylenedichloride solvate form V and the typical form V x-ray powder diffraction spectrum of aripiprazole ethylenedichloride solvate form V is shown in FIG. 3.

Aripiprazole ethylenedichloride solvate form V is characterized by peaks in the powder x-ray diffraction spectrum having 2θ angle positions at about 10.7, 17.6, 17.8, 20.6, 22.1, 23.4, 24.7 and 26.4 degrees.

In accordance with the present invention, there is provided a process for preparation of the Aripiprazole ethylenedichloride solvate form V comprising the steps of:

a) preparing a solution of aripiprazole in ethylenedichloride and
b) isolating aripiprazole ethylenedichloride solvate form V from the solution.

The solution of aripiprazole is usually prepared at elevated temperature, preferably at reflux temperature and then the solution is cooled preferably to 0° C. to 30° C. The precipitated form V crystals are collected by filtration or centrifugation.

Aripiprazole aripiprazole ethylenedichloride solvate can be used to prepare aripiprazole forms by crystallizing from the appropriate solvent system. Thus, for example aripiprazole form III can be prepared by preparing a solution of aripiprazole ethylenedichloride in a mixture of methyl tert-butyl ether, acetonitrile and tetrahydrofuran and isolating aripiprazole form III from the solution.

In accordance with the present invention, there is provided a pharmaceutical composition comprising aripiprazole form III and a pharmaceutically acceptable carrier or diluent.

Figure 1:
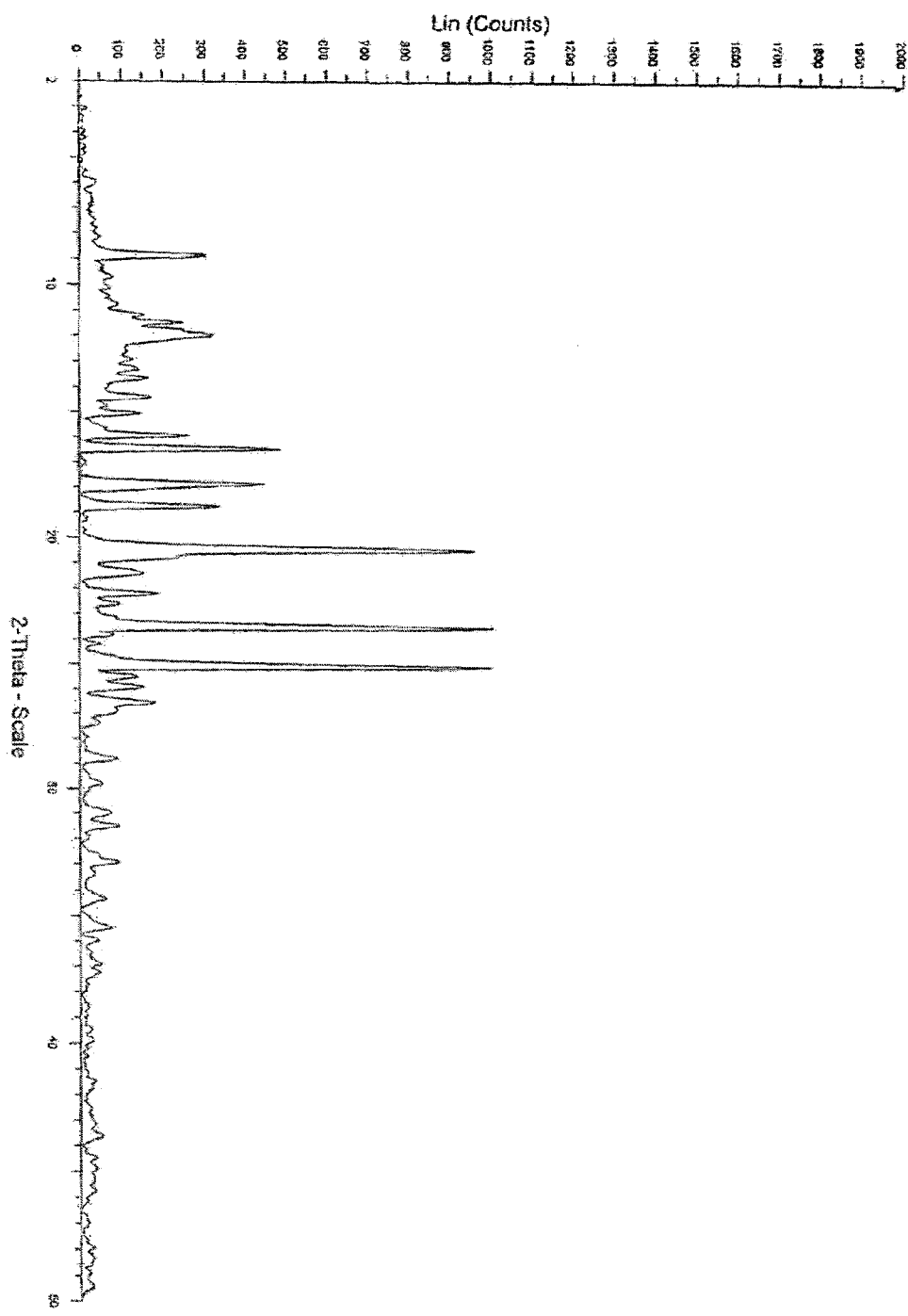
FIG. 1 is a x-ray powder diffraction spectrum of aripiprazole form III.
Figure 2:
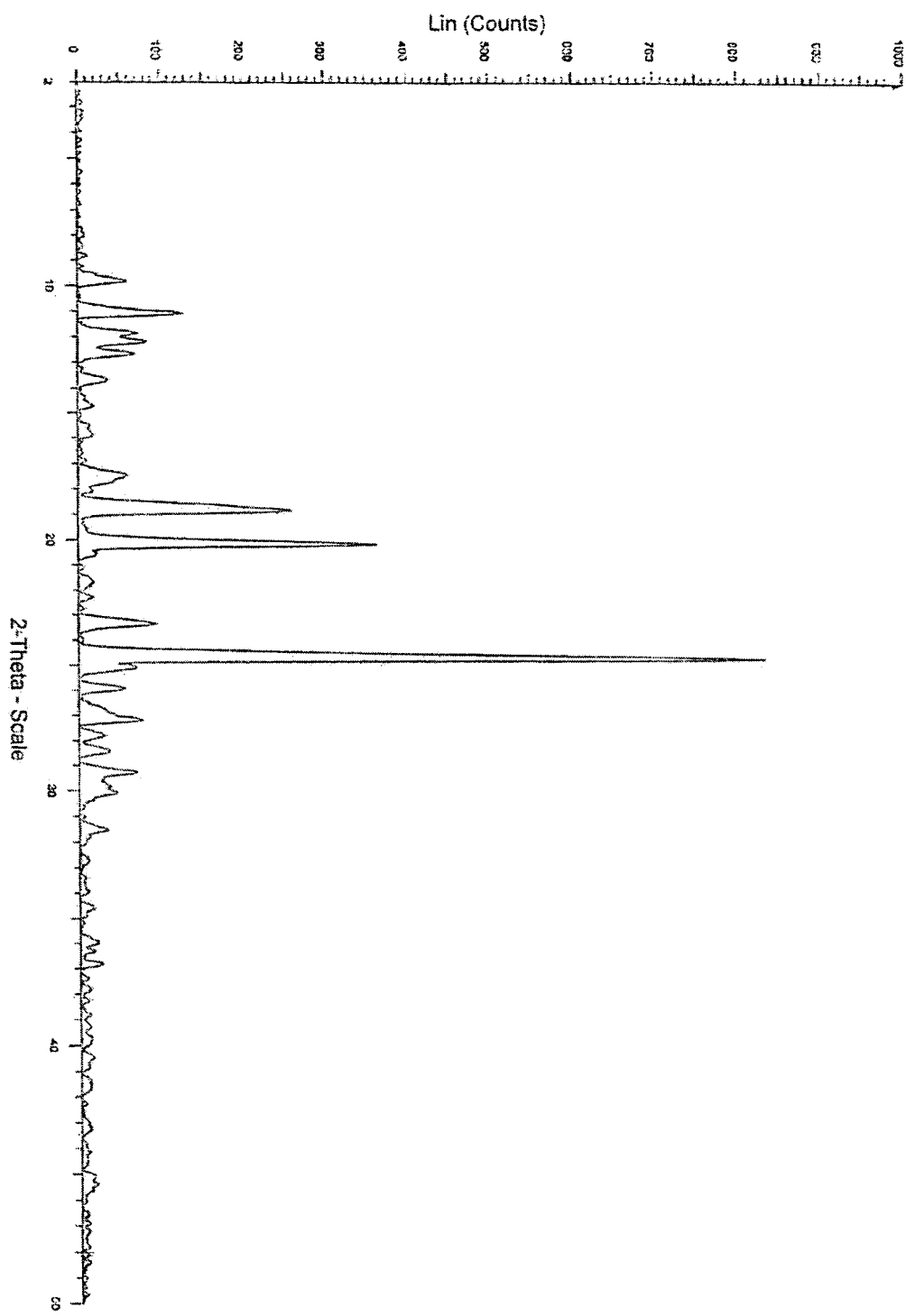
FIG. 2 is a x-ray powder diffraction spectrum of aripiprazole methanolate form IV.
Figure 3:
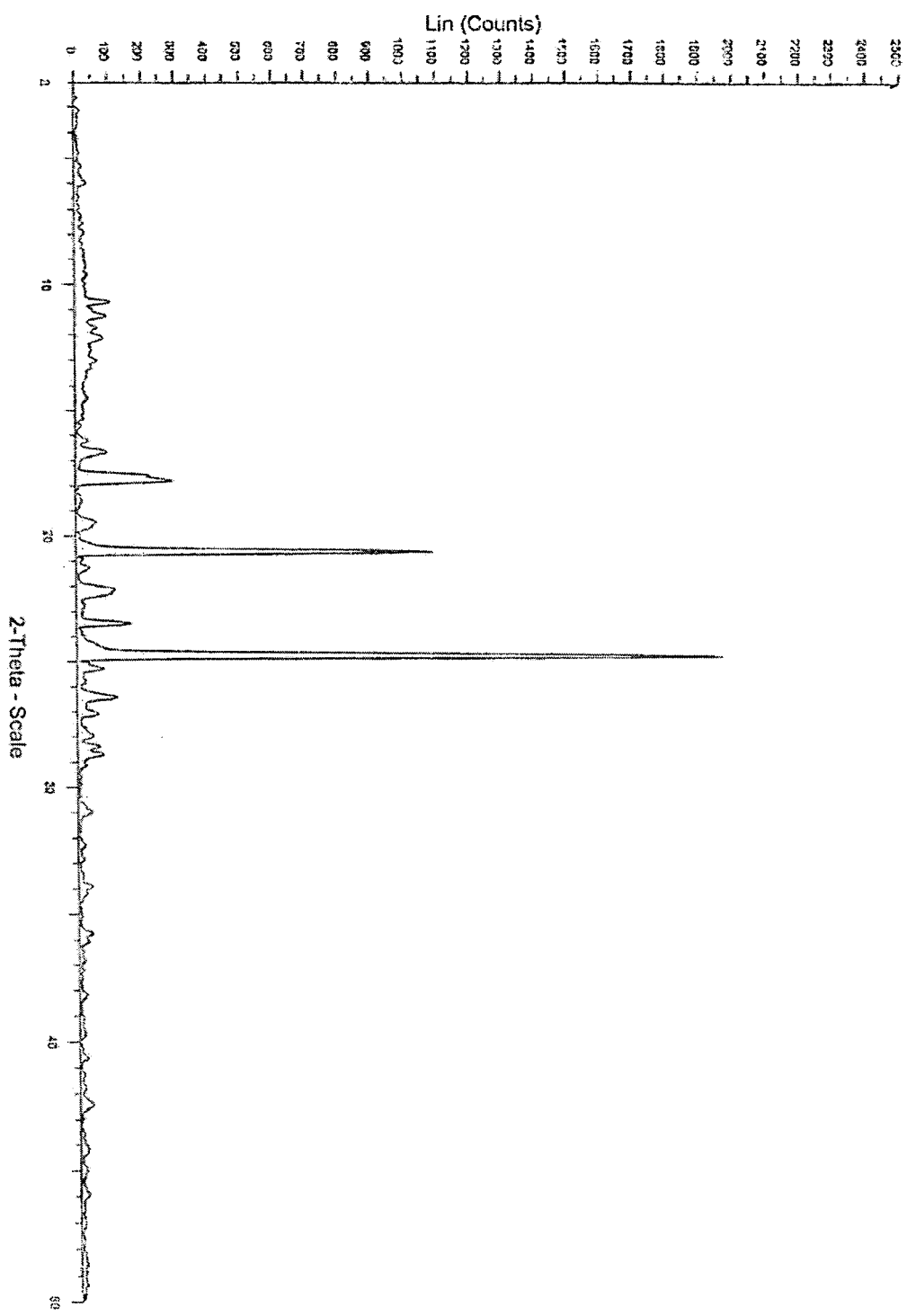
FIG. 3 is a x-ray powder diffraction spectrum of aripiprazole ethylenedichloride solvate form V.

x-Ray powder diffraction spectrum was measured on a Bruker axs D8 advance x-ray powder diffractometer having a copper-Kα radiation.

The invention will now be further described by the following examples, which are illustrative rather than limiting.

EXAMPLE 1

Aripiprazole (3 gm) is mixed with methyl tert-butyl ether (25 ml) and heated to reflux temperature. Then acetonitrile (45 ml) and tetrahydrofuran (25 ml) are added to the mixture and heated to about 55° C. to form a clear solution. The solution is slowly cooled to 25° C., stirred for 1 hour at about 25° C. and the precipitated crystals are collected by filtration to give 2 gm of aripiprazole form III.

EXAMPLE 2

Aripiprazole (3 gm), obtained by a known method is mixed with methanol (30 ml) and heated to reflux temperature. Then tetrahydrofuran (25 ml) is added at the same temperature to form a clear solution. The solution is slowly cooled to about 25° C., stirred for 1 hour at about 25° C. and the separated crystals are collected by filtration to give 2.9 gm of aripiprazole methanolate form IV.

EXAMPLE 3

Example 1 is repeated using aripiprazole methanolate obtained as in example 2 instead of aripiprazole to give aripiprazole form III.

EXAMPLE 4

Aripiprazole (3 gm) is mixed with ethylenedichloride (30 ml) and heated to 50° C. to form a clear solution. The solution is slowly cooled to 25° C., stirred for 1 hour at about 25° C. and the separated crystals are collected by filtration to give 2.5 gm of aripiprazole ethylenedichloride solvate form V.

EXAMPLE 5

Example 1 is repeated using aripiprazole ethylenedichloride solvate obtained as in example 4 instead of aripiprazole to give aripiprazole form III.

We claim:

1. Aripiprazole methanolate.
2. Aripiprazole methanolate of claim 1, wherein methanol content is between about 2 to 6% of the weight of aripiprazole methanolate.
3. A process for preparation of aripiprazole methanolate, which comprises the steps of:
   a) preparing a solution of aripiprazole in a mixture of methanol and tetrahydrofuran; and
   b) isolating aripiprazole methanolate from the solution.

\* \* \* \* \*